(12) United States Patent
Pond

(10) Patent No.: US 6,464,498 B2
(45) Date of Patent: Oct. 15, 2002

(54) IRRIGATION AND ASPIRATION HANDPIECE

(76) Inventor: Gary J. Pond, 2816 N. Main St., Racine, WI (US) 53402

(*) Notice: Subject to any disclaimer, the term of this patent is extended or adjusted under 35 U.S.C. 154(b) by 0 days.

(21) Appl. No.: 09/818,076

(22) Filed: Mar. 27, 2001

(65) Prior Publication Data
US 2002/0142260 A1 Oct. 3, 2002

(51) Int. Cl.[7] ................................................ A61C 5/02
(52) U.S. Cl. ............................ 433/81; 433/91; 604/22
(58) Field of Search ........................... 433/80, 81, 91, 433/224; 604/22

(56) References Cited

U.S. PATENT DOCUMENTS

| | | | | |
|---|---|---|---|---|
| 611,136 | A | 9/1898 | Mason | 206/538 |
| 1,672,114 | A | 6/1928 | Crow | 604/249 |
| RE21,187 | E | 8/1939 | Hooper | 604/249 |
| 2,214,230 | A | 9/1940 | Freeburg | 206/723 |
| 2,557,222 | A | 6/1951 | Goode | 206/365 |
| 2,711,586 | A | 6/1955 | Groves | 433/95 |
| 2,756,740 | A | 7/1956 | Deane | 604/249 |
| 2,812,765 | A | 11/1957 | Tofflemire | 604/32 |
| 2,929,510 | A | 3/1960 | Penn | 206/366 |
| 2,985,285 | A | 5/1961 | Riddle | 206/366 |
| 3,164,153 | A | 1/1965 | Zorzi | 433/88 |
| 3,208,145 | A | 9/1965 | Turner | 433/95 |
| 3,593,423 | A | 7/1971 | Jones et al. | 433/80 |
| 3,624,907 | A | 12/1971 | Brass et al. | 433/81 |
| 3,640,304 | A | 2/1972 | Fox et al. | 433/80 |
| 3,645,497 | A | 2/1972 | Nyboer | 433/95 |
| 3,727,310 | A | 4/1973 | Baker | 433/80 |
| 3,816,921 | A | * 6/1974 | Malmin | 433/81 |
| 4,021,921 | A | * 5/1977 | Detaille | 433/81 |
| 4,106,198 | A | 8/1978 | Childress | 433/28 |
| 4,215,476 | A | 8/1980 | Armstrong | 433/80 |
| 4,227,878 | A | 10/1980 | Lohn | 433/80 |
| 4,253,831 | A | 3/1981 | Eaton, II | 433/91 |
| 4,340,365 | A | 7/1982 | Pisanu | 433/80 |
| 4,353,694 | A | 10/1982 | Pelerin | 433/77 |
| 4,397,640 | A | 8/1983 | Haug et al. | 604/33 |
| 4,526,573 | A | 7/1985 | Lester et al. | 604/33 |
| 4,552,531 | A | 11/1985 | Martin | 433/147 |
| 4,578,055 | A | 3/1986 | Fischer | 604/2 |
| 4,752,444 | A | 6/1988 | Bowen et al. | 422/28 |
| D302,586 | S | 8/1989 | Zogg et al. | D24/15 |
| 4,872,837 | A | 10/1989 | Issalene et al. | 433/29 |
| 5,044,953 | A | 9/1991 | Sullivan | 433/92 |
| 5,052,927 | A | 10/1991 | Discko, Jr. | 433/90 |
| 5,057,283 | A | 10/1991 | Guggenheim et al. | 422/16 |
| 5,061,180 | A | 10/1991 | Wiele | 433/91 |
| 5,087,198 | A | 2/1992 | Castellini | 433/80 |
| 5,171,146 | A | 12/1992 | Guerci | 433/81 |
| 5,204,004 | A | 4/1993 | Johnson et al. | 433/80 |
| 5,230,704 | A | 7/1993 | Moberg et al. | 604/34 |
| 5,236,356 | A | 8/1993 | Davis et al. | 433/80 |
| 5,289,919 | A | 3/1994 | Fischer | 206/571 |
| 5,295,825 | A | * 3/1994 | Grosrey | 433/81 |
| 5,318,443 | A | 6/1994 | Overmyer | 433/104 |
| 5,348,711 | A | 9/1994 | Johnson et al. | 422/300 |
| 5,378,149 | A | 1/1995 | Stropko | 433/80 |
| 5,378,150 | A | 1/1995 | Harrel | 433/91 |

(List continued on next page.)

OTHER PUBLICATIONS

Kent Dental —Spring / Summer 1984 Product Catalog —p. 153–154.

*Primary Examiner*—John J. Wilson
(74) *Attorney, Agent, or Firm*—Ryan Kromholz & Manion, S.C.

(57) ABSTRACT

An assembly for aspirating and irrigating an endodontic or other cavity. The assembly includes a handpiece having at least one fluid discharge inlet and a vacuum outlet. The assembly further includes a surgical needle connected to the handpiece by way of a L-shaped connector. The L-shaped connector is arranged to support the needle while concurrently providing communication between a fluid discharge tube and an aspiration tubing.

4 Claims, 5 Drawing Sheets

U.S. PATENT DOCUMENTS

| | | | |
|---|---|---|---|
| 5,419,772 A | 5/1995 | Teitz et al. | 604/141 |
| 5,468,148 A | 11/1995 | Ricks | 433/80 |
| 5,474,450 A | 12/1995 | Chronister | 433/80 |
| 5,526,841 A | 6/1996 | Detsch et al. | 137/15 |
| 5,554,026 A | 9/1996 | Van Hale | 433/82 |
| 5,556,279 A | 9/1996 | Wolf et al. | 433/82 |
| 5,593,304 A | 1/1997 | Ram | 433/82 |
| 5,658,144 A | 8/1997 | Tinder et al. | 433/80 |
| 5,716,210 A | 2/1998 | Novak | 433/82 |
| 5,772,433 A | 6/1998 | Esrock | 433/80 |
| 5,837,204 A | 11/1998 | Prevost et al. | 422/105 |
| 5,853,384 A * | 12/1998 | Bair | 604/22 |
| 5,876,201 A | 3/1999 | Wilson et al. | 433/80 |
| 5,899,692 A | 5/1999 | Davis et al. | 433/80 |
| 5,947,990 A * | 9/1999 | Smith | 604/22 |

* cited by examiner

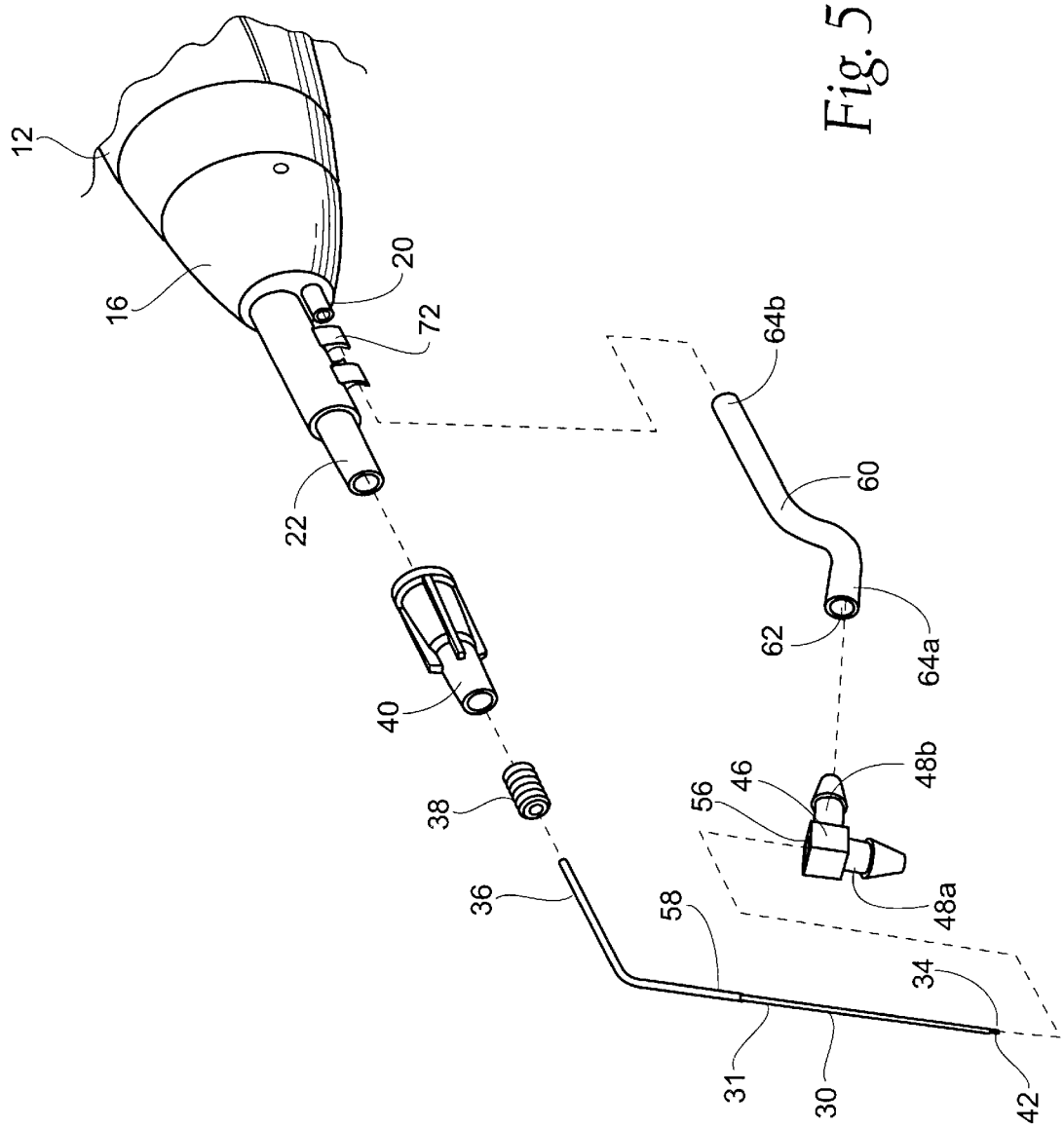

IRRIGATION AND ASPIRATION HANDPIECE

BACKGROUND OF THE INVENTION

This invention relates to multipurpose dental handpieces, and in particular, handpieces which irrigate and aspirate during endodontic procedures, such as root canal surgery. During endodontic procedures, such as root canals, it is necessary to inject or applicate fluid into the dental pulp or root. Additionally, debris and other matter must be removed from the dental cavity. Presently, typical handpieces used for these types of procedures are designed to spray fluid, under positive pressure, into the tooth cavity. This arrangement has been known to cause a number of difficulties, most notably damage to the tooth cavity caused by undue fluid force.

During a typical root canal procedure, a dental practitioner drills an opening in a patient's tooth surface enamel and inner dentine to gain access to the dental pulp and surrounding cavity. A hollow, surgical needle is inserted into the opening to both remove decaying pulp tissue by aspiration, and irrigate the cavity with sodium hypochlorite solution. The sodium hypochlorite solution rids the canal of bacteria and other foreign substances before sealant is injected into the canal. The dental pulp cavity is curvately elongate and tapers into the root area of the affected tooth. Common dental practice at this time includes the use of a handpiece fitted with a rigid, stainless steel needle whereby the practitioner alternatively aspirates and irrigates the canal. Several problems are encountered with this arrangement. First, since a stainless steel needle is relatively rigid with respect to the tooth canal and cavity, care must be taken not to puncture the tooth wall and surrounding jaw. Further, access to the extreme distal end of the curved root cavity is not possible due to the rigid nature of the needle. Additionally, the force by which fluid is discharged through the needle can create undue pressure on the tooth walls and surrounding tissue, making full aspiration and irrigation of the canal without damage extremely difficult.

SUMMARY OF THE INVENTION

It is therefore an object of this invention to provide an endodontic handpiece assembly capable of irrigating a root canal safely and accurately, while additionally providing aspiration. The handpiece of the invention is provided with means for irrigation and means for aspiration, wherein irrigation is supplied through gravity and surface tension feed. This arrangement lessens the unwanted effects of pressure-applied irrigation while providing the convenience of a dual purpose tool. A control mechanism is disposed on the handpiece, which controls whether fluid dispenses from a fluid discharge nozzle, aspirating vacuum is supplied to a aspiration nozzle, or a combination of irrigation and evacuation is performed.

The assembly further comprises an autoclavable endodontic needle assembly capable of curving to the configuration of a root canal while being inserted therein. The needle of the present assembly may be produced to be pre-bent to a desired angle; the preferred angle chosen is 45 degrees. The needle of the present invention may also be provided with an angle-adjustment sleeve around a portion of the needle to allow for manual adjustment of the pre-bent angle.

It is to be further noted that use of sodium hypochlorite solution as an irritant can be caustic and have an adverse affect on the preferred binary NiTi alloy of the needle. To substantially eliminate the possibility of the solution corroding or deteriorating the NiTi alloy, a coating, such as a parylene polymer, may be applied to the needle during its manufacture. While parylene polymers are the preferred coatings, there are other commercially available coatings that provide similar protection.

It is a further object of the present invention to provide a unique tip for the needle. The tip portion of the present invention includes a skived area at the most distal end of the needle. The skived area allows side venting and prevents vacuum buildup during aspiration of the root canal. The unique tip is further capable of functioning within the narrow and curved confines of a root canal.

The assembly is further provided with an L-shaped connector having two legs. The connector provides communicative connection between both the needle and the aspiration nozzle, and the needle and the discharge nozzle. Each leg of the connector includes a through bore which terminates in an aperture. A third aperture is provided intermediate the ends of the legs. The needle is attached to the handpiece by way of the L-shaped connector and an adhesive-filled supporting hub member which grippingly engages the needle shaft to provide connection to a conventional LUER® lock. The needle is positioned in one leg of the connector and through its bore, such that an attachment end of the needle is simultaneously positioned through the third aperture.

The needle shaft is thereby grippingly received in one bore leg while its attachment end extends through the third aperture where a supporting hub member supports the attachment end to provide connection with a conventional LUER® lock. The LUER® lock is adapted to be received by the aspiration nozzle by way of an interference fit.

The second leg of the L-shaped connector is adapted to receive a flexible tubing length having a through-bore. One end of the tubing is arranged to fit over the second leg aperture while the second end fits over the discharge nozzle. This arrangement allows communication between the discharge nozzle and the second leg of the L-shaped connector. As fluid flows from the discharge nozzle, through the second leg bore it encounters the needle shaft in position in the first leg bore. The fluid then moves out of the first leg aperture along the outside of the needle shaft. The fluid is drawn down the needle shaft and toward the needle tip by surface tension and gravity pull, rather than the positive pressure present in prior art arrangements.

DESCRIPTION OF THE DRAWINGS

FIG. 5 is an exploded view of the needle assembly and connector of the present invention.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

The term "fluid", as used herein, shall be defined as a gas, a liquid, a substance which flows, or a substance which differs from a solid in that it can offer no permanent resistance to change of shape. It shall further include mixtures of gases, mixtures of liquids, and mixtures of gases and liquids.

Figure 1:
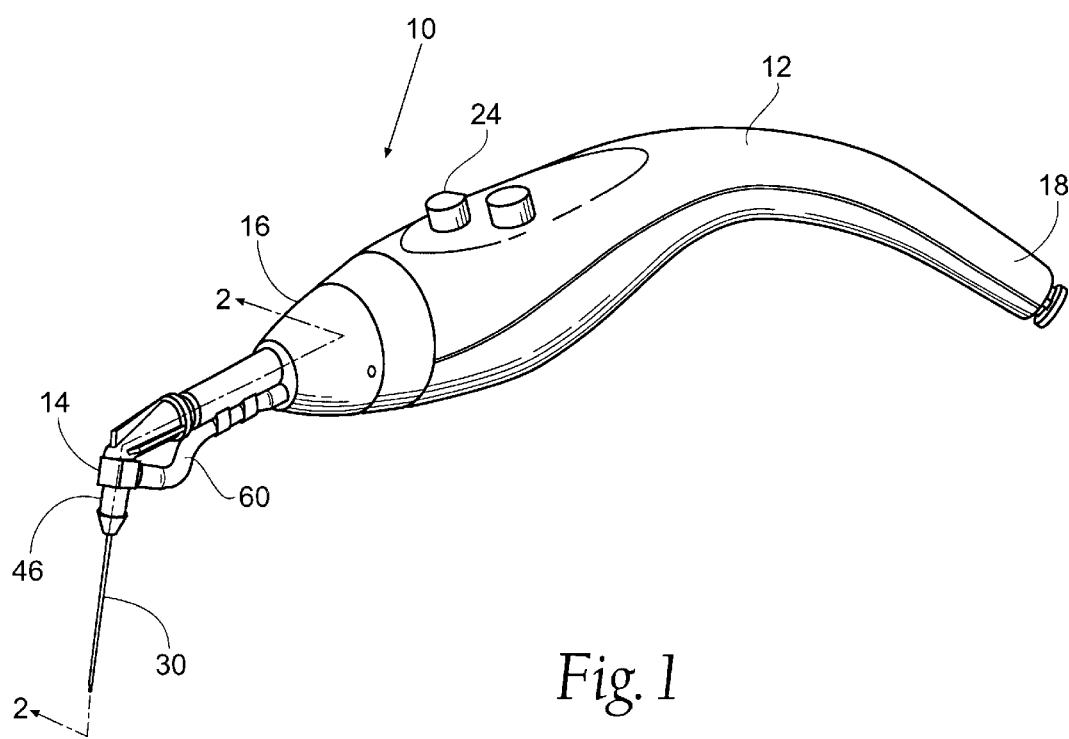
FIG. 1 is perspective view of the handpiece and needle of the present invention.
Figure 2:
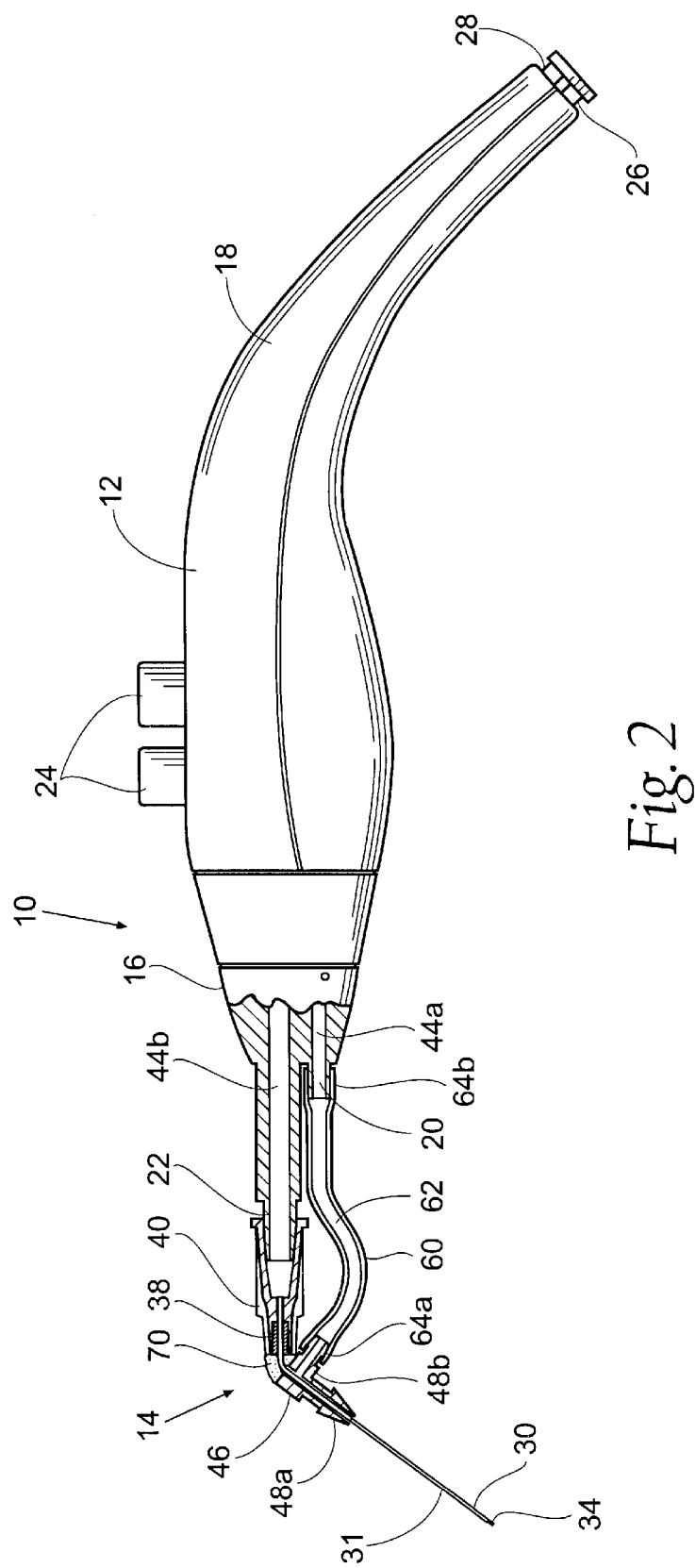
FIG. 2 is a partially cut-away cross sectional view taken along lines 2—2 of FIG. 1.

With reference to FIG. 1, an assembly 10 capable of dispensing fluids to and evacuating a cavity (not shown) during endodontic procedures is seen. The assembly 10 includes a handpiece 12 and a needle assembly 14. The handpiece 12 includes a distal end 16 and a proximal end 18, the proximal end 18 being adapted for facile gripping by a dental practitioner. As seen in FIG. 2, the distal end 16 includes a fluid discharge nozzle 20 and an aspiration nozzle 22. A control mechanism, seen as manual switch 24, is disposed on the handpiece 12. The control mechanism 24 controls whether fluid dispenses from the fluid discharge nozzle 20, aspirating vacuum is supplied to the aspiration nozzle 22, or a combination of irrigation and evacuation is performed. The switch 24 may also be provided with a finger-less lock-on feature that permits the switch to be maintained in an "on" position without the need for constant finger operation by the user. Alternatively, the handpiece may be provided with separate switches 24 for each aspiration or irrigation function. At least one fluid inlet 26 and one fluid outlet 28, are each disposed, preferably at the proximal end 18 of the handpiece 12.

The assembly 10 further comprises an autoclavable endodontic needle assembly 14. As seen particularly in the views of FIGS. 2–5, the needle assembly 14 includes a surgical needle 30 having a shaft 31 including a hollow bore 32, a tip portion 34 and an end attachment portion 36. The needle 30 is preferably mounted on a hub member or hub apparatus 38. The hub apparatus 38 is preferably provided with a cup-like interior and is arranged for mating arrangement with a conventional LUER® connector 40. The connector 40 is also commonly referred to as a slip LUER® or a LUER® lock fitting. The hub apparatus 38 is molded from autoclavable material, such as Ultim 1000, obtainable from General Electric Corporation.

The needle 30 is preferably fabricated from a binary NiTi alloy, whereby the needle 30 is capable of curving to the configuration of a root canal while being inserted therein. The preferred binary NiTi alloy contains 55.8 weight percent Nickel. The needle 30 of the present needle assembly 14 may be produced to be pre-bent to a desired angle; the preferred angle chosen is 45 degrees. The needle 30 of the present invention may also be provided with an angle-adjustment sleeve 58, best seen in FIG. 5. The angle adjustment sleeve 58 may be arranged around a portion of the needle 30 shaft 31 to allow for manual adjustment of the pre-bent angle.

It is to be further noted that use of sodium hypochlorite solution as an irrigant can be caustic and have an adverse affect on the preferred binary NiTi alloy of the needle 30. To substantially eliminate the possibility of the solution corroding or deteriorating the NiTi alloy, a coating (not seen in these views), such as a parylene polymer, may be applied to the needle 30 during its manufacture. While parylene polymers are the preferred coatings, there are other commercially available coatings that provide similar protection. The coating inhibits the sodium hypochlorite solution from adversely affecting the physical properties of the dental needle 30.

The tip portion 34 of the needle 30 of the present assembly 10 preferably includes a skived area 42. The skived area 42 allows side venting and prevents vacuum buildup during aspiration of the root canal (not shown). The unique tip 34 is further capable of functioning within the narrow and curved confines of a root canal.

As seen in FIG. 2, the handpiece 12 is preferably adapted to contain two fluid passageways 44a, 44b. The first passageway or fluid draw line 44a provides a pathway for fluid moving from a fluid source (not shown) to the discharge nozzle 20. The second passageway 44b provides a pathway for evacuation of fluid and debris from the distal end or tip 34 of the needle 30 to a outlet reservoir or vacuum source (not shown).

Figure 3:
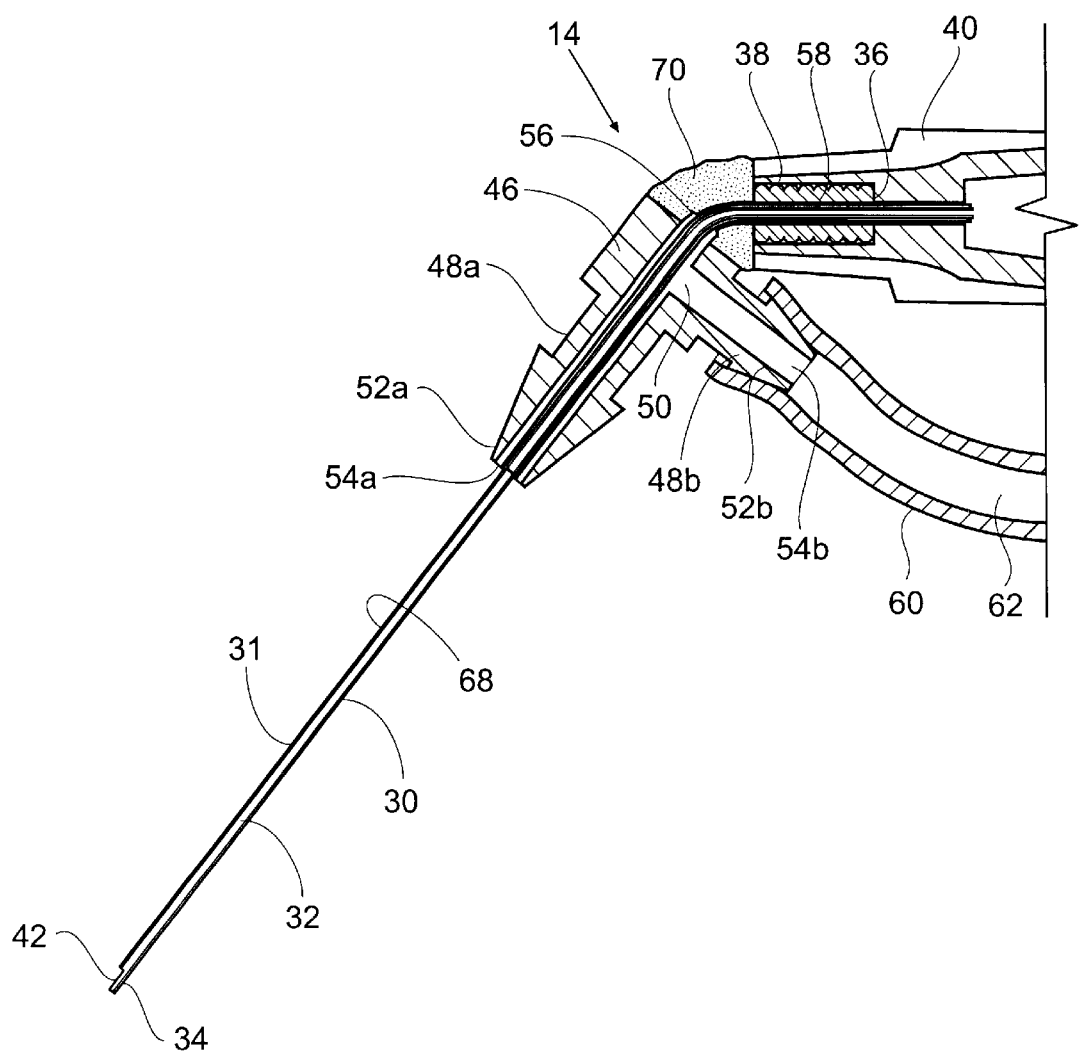
FIG. 3 is an enlarged view of the cross sectional area seen in FIG. 2.
Figure 4:
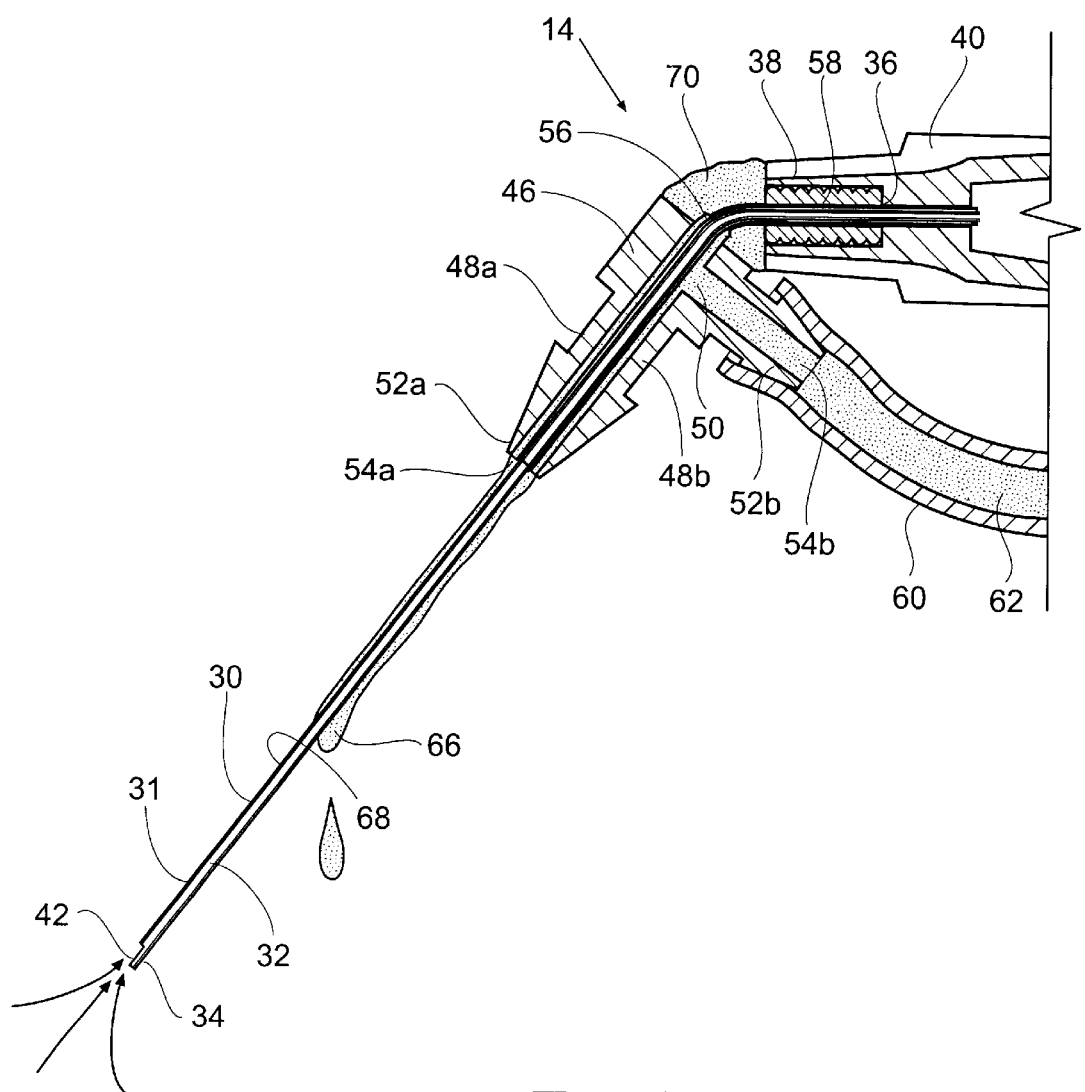
FIG. 4 is a view similar to the view of FIG. 3, but showing the general direction of irrigation fluid traveling on the outer surface of the needle shaft and toward the distal end of the needle, and the direction of aspiration into the bore of the needle.

As seen more particularly in FIGS. 3–5, the assembly 10 is further provided with an L-shaped connector 46 having a first leg 48a and a second leg 48b. The L-shaped connector 46 includes a through-bore 50 which is arranged to provide passageway through the first leg 48a and the second leg 48b. Each of the legs 48a, 48b terminate at a respective distal end 52a, 52b, each distal end includes a respective-leg aperture 54a, 54b communicating with the bore 50. A third aperture 56 is arranged intermediate the ends 52a, 52b of the legs 48a, 48b. The third aperture 56 is further arranged for communication with the L-shaped through-bore 50.

The needle 30 is attached to the handpiece 12 by way of the L-shaped connector 46 and the adhesive-filled supporting hub member 38 which grippingly engages the needle shaft 32 to provide connection to a conventional LUER® lock 40. The needle 30 is positioned in the first leg aperture 54a and through the first leg 48a of the through-bore 50, such that the attachment end 36 of the needle 30 is simultaneously positioned through the third aperture 56. Additional adhesive 70 may be used to seal the area around the third aperture 56 and needle attachment end 36. The needle shaft 32 is thereby grippingly received in the first bore leg 48a, while the attachment end 36 extends through the third aperture 56 and is supported by the supporting hub member 38 to provide connection with a conventional LUER® lock 40. The LUER® lock 40 is adapted to be received by the aspiration nozzle 22 (seen in FIG. 2), thereby completing the connection from aspiration nozzle 22 to needle tip 34 by way of the L-shaped connector.

The second leg 48b of the L-shaped connector 46 is adapted to receive a flexible tubing length 60 having a through-bore 62. As best viewed in FIGS. 2 and 5, the flexible tubing length 60 includes two ends 64a, 64b. The first end 64a is arranged to fit over the second leg 48b of the connector 46, while the second end 64b fits over the discharge nozzle 20 of handpiece 12. This arrangement allows communication between the discharge nozzle 20 and the second leg 48b of the L-shaped connector 46. The handpiece may optionally be provided with tubing clips 72, seen in FIG. 5, to aid in positioning the tubing length 60 between the fluid discharge nozzle 20 and the second leg 48b of the L-shaped connector 46.

As illustrated particularly in FIG. 4, when fluid discharge is desired, fluid 66 flows from the discharge nozzle 20, of the handpiece 12 and through the tubing 60 bore 62. The fluid 66 continues through the second leg 48b bore 50 until it encounters the needle shaft 32 in position in the first leg 48a bore 50. The fluid 66 then moves out the first leg aperture 54a along the outer surface 68 of the needle shaft 32. The fluid 66 is drawn down along the outer surface 68 of the needle shaft 32 and toward the needle tip 34 through surface tension and gravity pull, rather than the positive pressure present in prior art arrangements.

During fluid discharge, the outer surface 68 of the needle shaft 32 acts as a conduit to direct the fluid 66 toward a desired irrigation site, such as a dental cavity (not shown). Aspiration of the site is done through the needle bore 32, as indicated by the arrows in FIG. 4. The bore 32 of the needle 30 communicates with the LUER® connector 40 which allows the aspirate (not shown) to be carried through the aspiration nozzle 22 and out the fluid outlet 28 (seen in FIG. 1).

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. An assembly for dispensing fluids and for evacuating a cavity during an endodontic procedure, the assembly comprising:
    a handpiece including means for fluid discharge and means for evacuation;
    at least one inlet and at least one outlet disposed on said handpiece;
    a control mechanism disposed on said handpiece, the control mechanism controlling discharge and evacuation to and from said handpiece;
    a surgical needle having a hollow shaft connected to said handpiece;
    a connector communicating with said means for fluid discharge and said means for evacuation; and
    said connector further including means for communicating with and supporting a surgical needle, said needle further including an external surface substantially coextensive of its length and a coextensive bore, said bore being arranged to communicate with said means for evacuation; said external surface of said needle being arranged for transport of a selected irrigation fluid, said irrigation fluid being transported along said external surface of said needle by way of needle surface tension and gravity.

2. The assembly of claim 1 wherein said external surface of said needle is arranged to communicate with said connector and said means for discharge.

3. The assembly of claim 1 wherein said connector is L-shaped and includes first and second communicating hollow legs, each of said legs defining a coextensive bore.

4. The assembly of claim 3 wherein said hollow needle is located in one of said coextensive bores, said one of said coextensive bores communicating with said inlet of said handpiece.

\* \* \* \* \*